(12) United States Patent
Guo et al.

(10) Patent No.: US 11,925,819 B2
(45) Date of Patent: Mar. 12, 2024

(54) TREATMENT COUCH AND RADIOTHERAPY SYSTEM

(71) Applicants: SHENZHEN OUR NEW MEDICAL TECHNOLOGIES DEVELOPMENT CO., LTD., Shenzhen (CN); OUR UNITED CORPORATION, Shaanxi (CN)

(72) Inventors: Zhao Guo, Shenzhen (CN); Hongbin Zhao, Shenzhen (CN); Yueming Yang, Shenzhen (CN)

(73) Assignees: SHENZHEN OUR NEW MEDICAL TECHNOLOGIES DEVELOPMENT CO., LTD., Shenzhen (CN); OUR UNITED CORPORATION, Xi'an (CN)

(*) Notice: Subject to any disclaimer, the term of this patent is extended or adjusted under 35 U.S.C. 154(b) by 428 days.

(21) Appl. No.: 17/238,978

(22) Filed: Apr. 23, 2021

(65) Prior Publication Data
US 2021/0236857 A1    Aug. 5, 2021

Related U.S. Application Data

(63) Continuation-in-part of application No. PCT/CN2019/089895, filed on Jun. 3, 2019.

(30) Foreign Application Priority Data

Oct. 24, 2018  (CN) .................. 201811244308.5

(51) Int. Cl.
   *A61N 5/10*    (2006.01)
(52) U.S. Cl.
   CPC .... *A61N 5/1082* (2013.01); *A61N 2005/1097* (2013.01)

(58) Field of Classification Search
   CPC .................. A61N 5/1082; A61N 2005/1097
   See application file for complete search history.

(56) References Cited

U.S. PATENT DOCUMENTS

| | | | |
|---|---|---|---|
| 6,094,760 A | | 8/2000 | Nonaka et al. |
| 2013/0025055 A1* | | 1/2013 | Saracen ............... A61N 5/1049 901/29 |

FOREIGN PATENT DOCUMENTS

| | | | | |
|---|---|---|---|---|
| CN | 102551785 A | | 7/2012 | |
| CN | 202960546 U | | 6/2013 | |
| CN | 205758589 U | | 12/2016 | |
| CN | 108079445 A | | 5/2018 | |
| CN | 108310681 A | | 7/2018 | |
| CN | 110234396 B | * | 2/2022 | ............... A61N 5/00 |

OTHER PUBLICATIONS

International Search Report and Written Opinion issued in corresponding International Application No. PCT/CN2019/089895 dated Aug. 30, 2019, with English translation.

* cited by examiner

*Primary Examiner* — David P Porta
*Assistant Examiner* — Fani Polyzos Boosalis
(74) *Attorney, Agent, or Firm* — Morgan, Lewis & Bockius LLP

(57) ABSTRACT

The treatment couch includes a couch panel, a main supporting structure, an auxiliary supporting structure and a supporting beam. Both ends of the supporting beam are respectively connected to the main supporting structure and the auxiliary supporting structure.

15 Claims, 4 Drawing Sheets

TREATMENT COUCH AND RADIOTHERAPY SYSTEM

CROSS-REFERENCE TO RELATED APPLICATION

This application is a Bypass Continuation-in-Part Application of PCT/CN2019/089895, filed on Jun. 3, 2019, which claims priority to Chinese Patent Application No. 201811244308.5, filed on Oct. 24, 2018, which are incorporated herein by reference in their entirety.

TECHNICAL FIELD

The disclosure relates to the technical field of medical apparatuses, and in particular, to a treatment couch and a radiotherapy system.

BACKGROUND

Radiation therapy is an important means of treating cancer, and large-scale radiation therapy apparatuses are key medical apparatuses to conduct the radiation therapy. At present, gamma knives and medical linear accelerators are mainstream radiation therapy apparatuses of treating cancer, a gamma focusing therapy head or a therapy head of the medical linear accelerator therapy head is installed on a frame, and beam axes of the therapy head intersect at isocenter of the frame. A patient is fixed on the treatment couch, and driven by the treatment couch to move, so that lesion portions of the patient are sent to the isocenter for treatment. With the advancement of science and technology, radiation therapy enters an era of precision treatment and requires precise position, precise planning and precise treatment. The improvement of treatment accuracy requires a high-precision treatment couch to achieve accurate position of the patient's lesion portions.

The treatment couch of the radiotherapy apparatus needs to reliably support the patient, and drive the patient to move, so that cancerous lesions of the patient are accurately positioned at the isocenter of the apparatus.

SUMMARY

In one aspect, the embodiments of the present disclosure provide a treatment couch. The treatment couch includes a couch panel, a main supporting structure, an auxiliary supporting structure and a supporting beam, and both ends of the supporting beam are respectively connected to the main supporting structure and the auxiliary supporting structure.

In another aspect, the embodiments of the present disclosure provide a radiotherapy system that includes a radiological device comprising an opening, and the treatment couches described above. Wherein, the supporting beam of the treatment couch is located in the opening, and the main supporting structure and the auxiliary supporting structure are arranged at both ends of the opening, respectively.

BRIEF DESCRIPTION OF THE DRAWINGS

In order to more clearly illustrate the embodiments of the present invention or the technical solutions in the prior art, the drawings used in the description of the embodiments or the prior art will be briefly described below. Obviously, the drawings in the following description are only some embodiments of the present invention, and a person of ordinary skill in the art can obtain other drawings according to these drawings without paying any creative effort.

DETAILED DESCRIPTION

Figure 1:
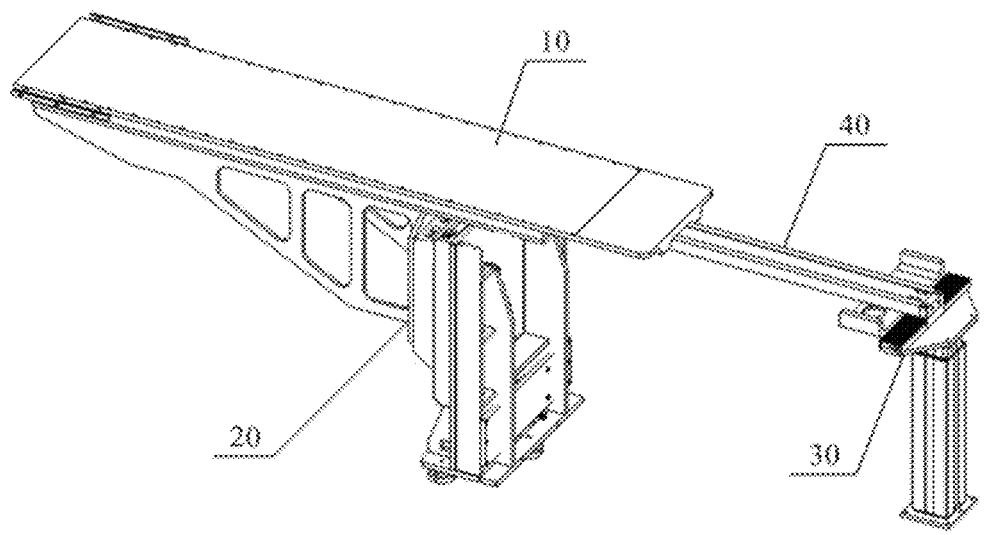
FIG. 1 is a first schematic diagram showing a structure of a treatment couch according to embodiments of the present disclosure.

Technical solutions in embodiments of the present disclosure will be described below clearly and completely with reference to the accompanying drawings. Obviously, the described embodiments are merely some but not all of embodiments of the present disclosure. All other embodiments obtained on a basis of the embodiments of the present disclosure by a person of ordinary skill in the art without paying any creative effort shall be included in the protection scope of the present disclosure.

It should be understood that in the description of the present disclosure, orientation or positional relationships indicated by terms "centre", "upper", "lower", "front", "rear", "left", "right", "vertical", "horizontal", "top", "bottom", "inner", "outer", etc. are based on orientations or relationships shown in the drawings, merely to facilitate and simplify the description of the present disclosure, but not to indicate or imply that the referred devices or elements must have a particular orientation, or must be constructed or operated in a particular orientation. Therefore it should not be construed as a limitation to the present disclosure.

Terms such as "first" and "second" are used for descriptive purposes only, and are not to be construed as indicating or implying the relative importance or implicitly indicating the number of technical features below. Thus, features defined with "first" and "second" may explicitly or implicitly include one or more of the features. In the description of the present disclosure, the term "a plurality of/the plurality of" means two or more unless otherwise specified.

In the description of the present disclosure, it will be noted that term "installed", "connected", or "attached" is be understood broadly. For example, it may be a fixed connection, a detachable connection, or an integral connection; and it may be a direct connection, or may be an indirect connection through an intermediate medium, or may be internal communication between two elements. Specific meanings of the above terms in the present disclosure may be understood by those skilled in the art according to specific situations.

Figure 2:
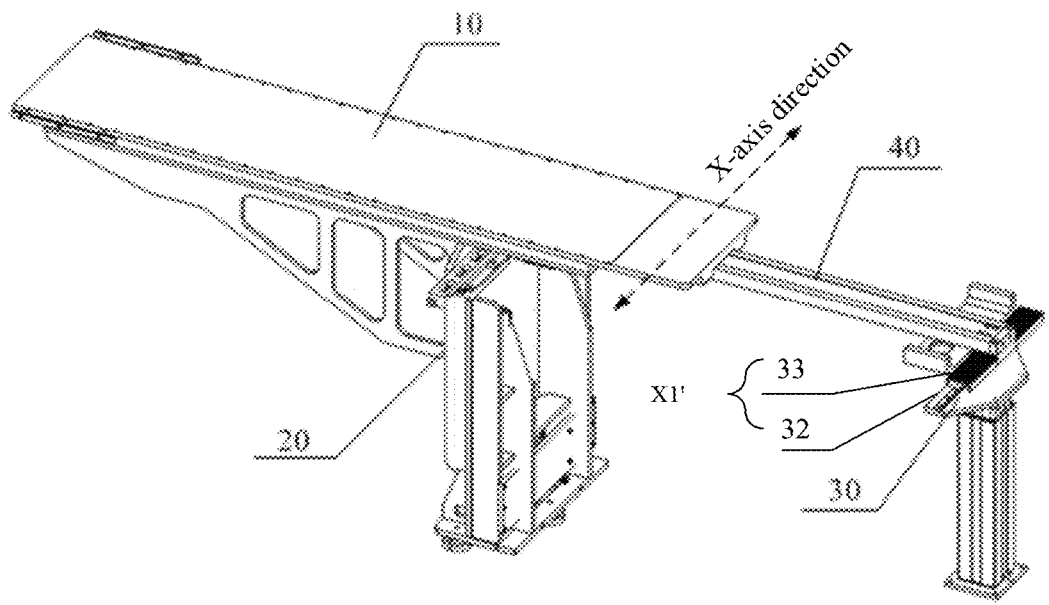
FIG. 2 is a second schematic diagram showing a structure of a treatment couch according to embodiments of the present disclosure.
Figure 3:
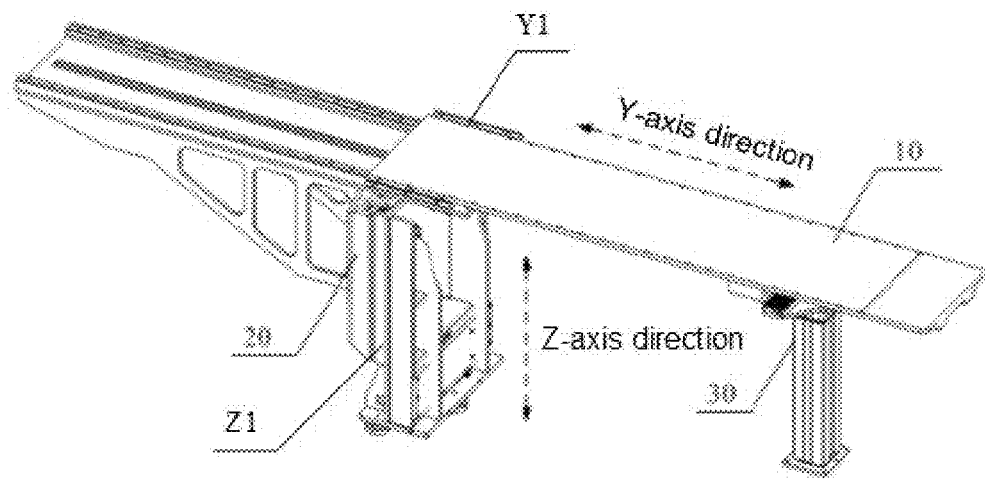
FIG. 3 is a third schematic diagram showing a structure of a treatment couch according to embodiments of the present disclosure.

Embodiments of the present disclosure provide a treatment couch. As shown in FIGS. 1 to 3, the treatment couch includes a couch panel 10, and further includes a main supporting structure 20, an auxiliary supporting structure 30 and a supporting beam 40. Both ends of the supporting beam 40 are respectively connected to the main supporting structure 20 and the auxiliary supporting structure 30. In some embodiments, the main supporting structure 20 is configured to drive the couch panel 10 to move towards the auxiliary supporting structure 30 along the supporting beam 40, so that the couch panel 10 is horizontally supported all the time during movement.

Figure 5:
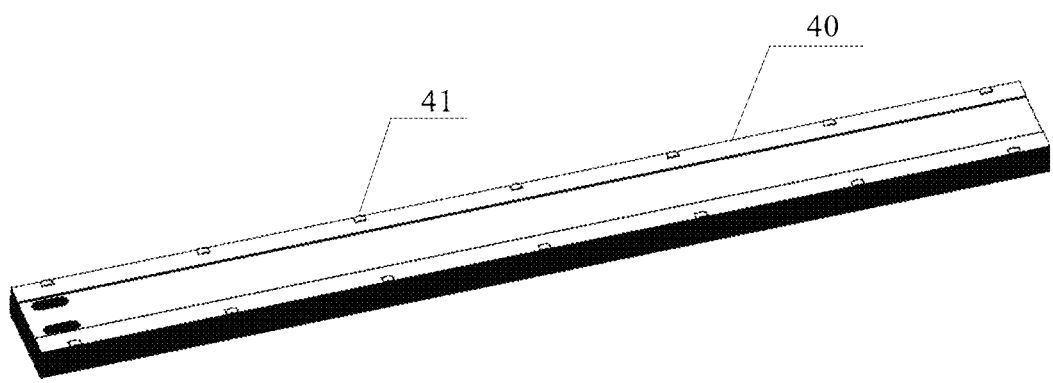
FIG. 5 is a first schematic diagram showing a structure of a supporting beam according to embodiments of the present disclosure.

Referring to FIGS. 1 to 3, the supporting beam 40 connects the main supporting structure 20 and the auxiliary supporting structure 30, and is used for supporting the couch panel 10 at all times during the movement of the couch panel 40 from the main supporting structure 20 to the auxiliary supporting structure 30. A specific shape, size and the like of the supporting beam 40 are not limited in the embodiments of the present disclosure, and may be set by those skilled in the art according to actual situations. Since the supporting beam 40 mainly plays a role of connection and support, and it is generally formed in a strip shape. For example, the supporting beam 40 may be in a rectangular strip shape as shown in FIG. 5.

Materials of manufacturing the couch panel 10 and the supporting beam 40 are not limited in the embodiments of the present disclosure. Since carbon fiber materials have good supporting strength, in practical applications, the carbon fiber material may be used for manufacturing the couch panel 10 and the supporting beam 40.

Since the supporting beam is provided between the main supporting structure and the auxiliary supporting structure in the treatment couch provided in the embodiments of the present disclosure, the supporting beam supports the couch panel in movement all the time during the movement of the couch panel from the main supporting structure to the auxiliary supporting structure. In this way, it is avoided that a large deformation of the couch panel occurs before the couch panel reaches the auxiliary supporting structure, which ensures a smooth connection between the couch panel and the auxiliary supporting structure, improves a precise positioning of lesion portions of the patient on the couch panel, and thereby improves the radiation therapy effect.

In some embodiments of the present disclosure, as shown in FIGS. 2 and 3, the main supporting structure 20 includes a Z-axis-direction moving component Z1 for driving the couch panel 10 to move in a Z-axis direction, a Y-axis-direction moving component Y1 for driving the couch panel 10 to move in a Y-axis direction and an X-axis-direction moving component X1 for driving the couch panel 10 to move in an X-axis direction. The Y-axis direction is an extending direction of the supporting beam 40, the Z-axis direction is a thickness direction of the supporting beam 40, and any two of the X-axis direction, the Y-axis direction, and the Z-axis direction are perpendicular to each other.

Exemplarily, the Z-axis-direction moving component Z1, Y-axis-direction moving component Y1 and X-axis-direction moving component X1 may be the same or different. In some embodiments, the Z-axis-direction moving component Z1, Y-axis-direction moving component Y1 and X-axis-direction moving component X1 are the same, and include a motor, a worm gear reducer and a screw rod. The screw rod is connected with the motor, the worm gear reducer and the couch panel 10, and the screw rod passes through the worm gear reducer. Through the drive of the motor, the screw rod rotates to drive the treatment couch to move.

The couch panel 10 may be moved freely in a three-dimensional space by providing the Z-axis-direction moving component Z1, the Y-axis-direction moving component Y1 and the X-axis-direction moving component X1. In this way, the flexibility of the movement of the couch panel 10 is improved, and lesion areas of the patient on the couch panel 10 can be better moved to an irradiation region for treatment.

Specific structures of the Z-axis-direction moving component Z1, the Y-axis-direction moving component Y1 and the X-axis-direction moving component X1 are not limited in the embodiments of the present disclosure, as long as the Z-axis-direction moving component Z1 can drive the couch panel 10 to move in the Z-axis direction, the Y-axis-direction moving component Y1 can drive the couch panel 10 to move in the Y-axis direction, and the X-axis-direction moving component X1 can drive the couch panel 10 to move in the X-axis direction.

Figure 4:
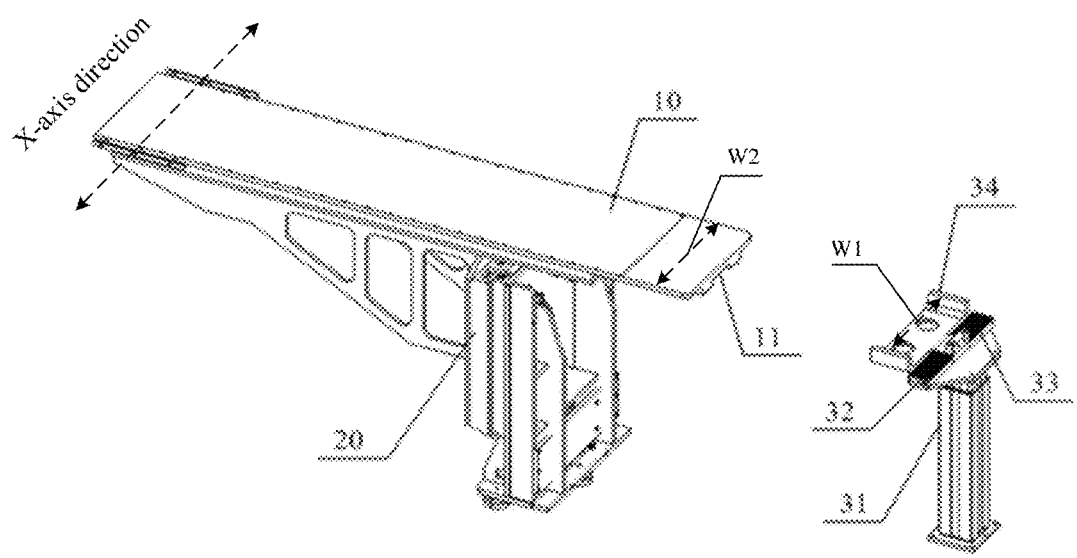
FIG. 4 is a fourth schematic diagram showing a structure of a treatment couch according to embodiments of the present disclosure.

Referring to FIGS. 2 and 4, in other embodiments of the present disclosure, the auxiliary supporting structure 30 includes a lifting member 31 for moving up and down synchronously with the Z-axis-direction moving component Z1, so as to support the couch panel 10 to move in the Z-axis direction.

A specific structure of the lifting member 31 is not limited in the embodiments of the present disclosure. For example, the lifting member 31 may be an electric lifting column, or may be a same structure as the Z-axis-direction moving component Z1. In some embodiments, the electric lifting column includes a lifting post body, transmission station and automatic detector. The lifting member 31 moves up and down synchronously with the Z-axis-direction moving component Z1 all the time to support the couch panel 10 together, so that the couch panel 10 is in a horizontal state all the time. In order to further improve a supporting accuracy, the supporting beam may also be provided with an adjustment structure, which may be used for adjusting a supporting level difference of the supporting beam before and after assembling thereof.

In some embodiments of the present disclosure, referring to FIG. 2 the auxiliary supporting structure 30 includes an X-axis-direction follow-up component X1', and the supporting beam 40 is connected with the X-axis-direction follow-up component X1', so that the couch panel 10 is moved in the X-axis direction. A specific structure of the X-axis-direction follow-up component X1' is not limited in the embodiments of the present disclosure. For example, the X-axis-direction follow-up component X1' may include a sliding rail 32 connected with the lifting member 31, and a sliding block 33 moving along the sliding rail 32. The sliding rail 32 is arranged in the X-axis direction, and the supporting beam 40 is connected with the sliding block 33.

Referring to FIG. 4, the sliding rail 32 and the sliding block 33 that cooperate with each other in the X-axis direction are provided on the lifting member 31. The sliding block 33 may be moved on the sliding rail 32 in the X-axis direction, and the supporting beam 40 is fixedly connected with the sliding block 33. When the couch panel 10 is moved in the X-axis direction, the supporting beam 40 may drive the sliding block 33 to move on the sliding rail 32.

As shown in FIG. 4, the auxiliary supporting structure 30 may also include a U-shaped tray 34 connected with the sliding block 33. The U-shaped tray 34 has a width W1 in the X-axis-direction that corresponds to a width W2 of the couch panel 10 in the X-axis-direction, so that the couch panel 10 may be extend into the U-shaped tray 34 under the drive of the Y-axis-direction moving component. The U-shaped tray 34 may limit the two sides in the X-axis-direction of the couch panel 10.

In other embodiments of the present disclosure, referring to FIG. 4, a bottom surface of the couch panel 10 is provided with a through groove 11 in a length direction of the couch panel 10, a portion of the supporting beam 40 is located in the through groove 11, and the through groove 11 may be located at a middle of the bottom surface of the couch panel 10 to ensure that the couch panel 10 is uniformly supported.

Figure 6:
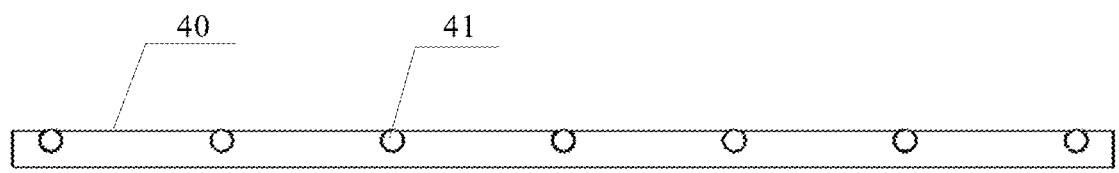
FIG. 6 is a second schematic diagram showing a structure of a supporting beam according to embodiments of the present disclosure.

Referring to FIGS. 5 and 6, opposite sides of the supporting beam 40 are provided with rollers 41 in a length direction of the supporting beam 40, and the rollers 41 are in contact with a bottom of the through groove 11. A specific number of rollers 41 is not limited in the embodiments of the present disclosure, and may be set by those skilled in the art according to actual situations.

By providing the rollers 41 in the supporting beam 40, in a case where the couch panel 10 is moved in the Y-axis direction, the couch panel 10 may be moved on the supporting beam 40 in a rolling manner, which may reduce resistance and wear.

Figure 7A:
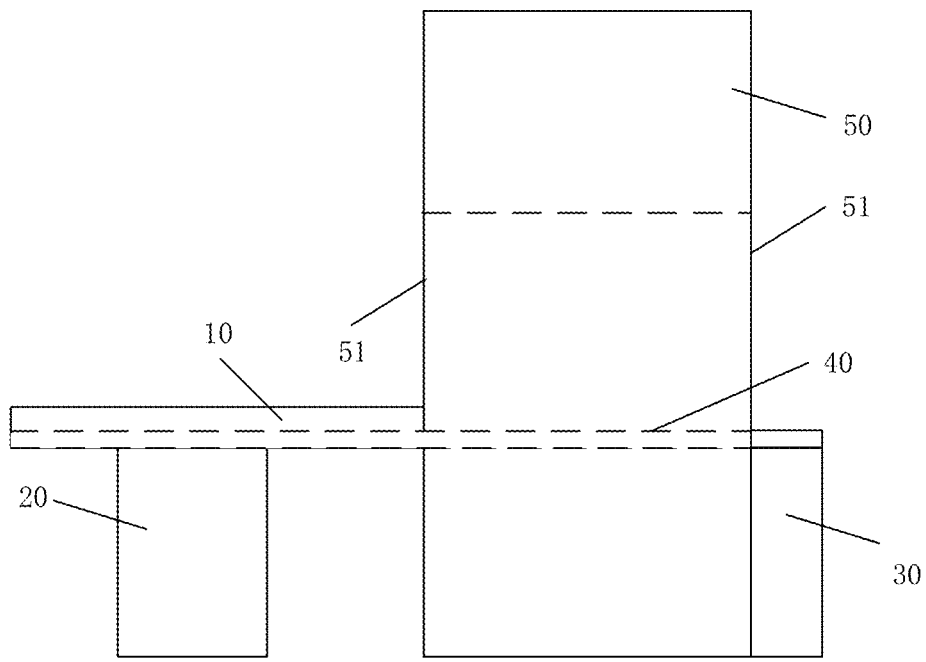
FIG. 7a is a schematic diagram of a radiotherapy system according to embodiments of the present disclosure.
Figure 7B:
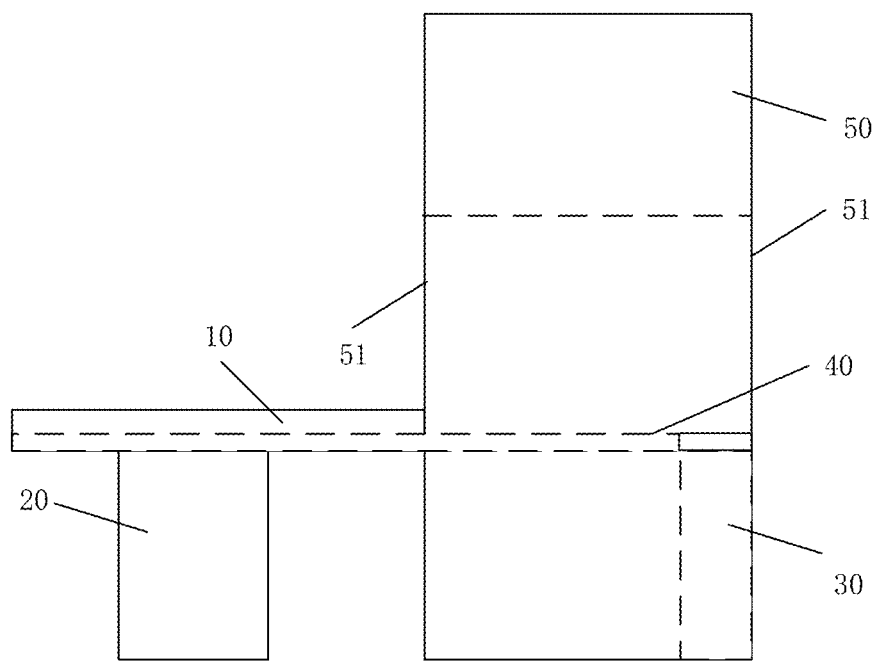
FIG. 7b is another schematic diagram of a radiotherapy system according to embodiments of the present disclosure.

Some embodiments of the present disclosure provide a radiotherapy system. As shown in FIG. 7a and FIG. 7b, the radiotherapy system includes a radiological device 50 including an opening 51, and the treatment couch as described in any of the above. A portion of the supporting beam 40 of the treatment couch is located in the opening 51, and the main supporting structure 20 and the auxiliary supporting structure 30 are arranged at both ends of the opening 51, respectively.

In some embodiments, the auxiliary supporting structure 30 is fixed with the radiological device 50. In some embodiments, the main supporting structure 20 is fixed with the radiological device 50.

In some embodiments, as shown in FIG. 7a, the auxiliary supporting structure 30 is located outside the opening 51. In some embodiments, as shown in FIG. 7b the auxiliary supporting structure 30 is located inside the opening 51.

In some embodiments, the main supporting structure 20 and the radiological device 30 are arranged independently of each other.

In the treatment couch and the radiotherapy system provided by the embodiments of the present disclosure, the treatment couch includes a couch panel, a main supporting structure, an auxiliary supporting structure, and a supporting beam, and both ends of the supporting beam are respectively connected to the main supporting structure and the auxiliary supporting structure. The main supporting structure is configured to drive the couch panel to move towards the auxiliary supporting structure along the supporting beam, so that the couch panel is horizontally supported all the time during movement. Since the supporting beam is provided between the main supporting structure and the auxiliary supporting structure in the treatment couch, the supporting beam supports the couch panel in movement all the time during the movement of the couch panel from the main supporting structure to the auxiliary supporting structure. In this way, it is avoided that a large deformation of the couch panel occurs before the couch panel reaches the auxiliary supporting structure, which ensures a smooth connection between the couch panel and the auxiliary supporting structure, improves a precise positioning of lesion portions of the patient on the treatment couch, and improves the radiation therapy effect.

The foregoing descriptions are merely some specific implementation manners of the present disclosure, but the protection scope of the present disclosure is not limited thereto, and the changes or replacements that any person skilled in the art can easily think of in the technical scope disclosed by the present disclosure should be within the protection scope of the present disclosure. Therefore, the protection scope of the present disclosure shall be subject to the protection scope of the claims.

What is claimed is:

1. A treatment couch, comprising:
   a couch panel;
   a main supporting structure;
   an auxiliary supporting structure; and
   a supporting beam, wherein
   both ends of the supporting beam are respectively connected to the main supporting structure and the auxiliary supporting structure;
   the supporting beam is located below the couch panel, so that the supporting beam is configured to support the couch panel all the time during movement of the couch panel; and
   the main supporting structure is configured to drive the couch panel to move towards the auxiliary supporting structure along the supporting beam, so that the couch panel is horizontally supported all the time during the movement.

2. The treatment couch according to claim 1, wherein the main supporting structure comprises a Z-axis-direction moving component for driving the treatment couch to move along a Z-axis direction, a Y-axis-direction moving component for driving the treatment couch to move along a Y-axis direction and an X-axis-direction moving component driving the treatment couch to move along an X-axis direction; wherein the Y-axis direction is an extending direction of the supporting beam, and any two of the X-axis direction, the Y-axis direction and the Z-axis direction are perpendicular to each other.

3. The treatment couch according to claim 2, wherein the auxiliary supporting structure comprises a lifting member for moving up and down synchronously with the Z-axis-direction moving component, so as to support the couch panel to move along the Z-axis direction.

4. The treatment couch according to claim 3, wherein the auxiliary supporting structure comprises an X-axis-direction follow-up component, and the supporting beam is connected with the X-axis-direction follow-up component, so that the couch panel is moved along the X-axis direction.

5. The treatment couch according to claim 4, wherein the X-axis-direction follow-up component comprises a sliding rail connected with the lifting member, and a sliding block moving along the sliding rail, the sliding rail is arranged along the X-axis direction, and the supporting beam is connected with the sliding block.

6. The treatment couch according to claim 5, wherein the auxiliary supporting structure further comprises a U-shaped tray connected with the sliding block, and the U-shaped tray has a width that corresponds to a width of the couch panel, so that the couch panel is capable of being extended into the U-shaped tray under the drive of the Y-axis-direction moving component.

7. The treatment couch according to claim 3, wherein the lifting member is an electric lifting column.

8. The treatment couch according to claim 1, wherein a bottom surface of the couch panel is provided with a through groove along a Y-axis direction, and a portion of the supporting beam is located in the through groove, wherein the Y-axis direction is an extending direction of the supporting beam.

9. The treatment couch according to claim 8, wherein opposite sides of the supporting beam are provided with rollers along a length direction of the supporting beam, and the rollers are in contact with a bottom of the through groove.

10. A radiotherapy system, comprising:
a radiological device comprising an opening, and
the treatment couch according to claim 1, wherein
a portion of the supporting beam of the treatment couch is located in the opening, and the main supporting structure and the auxiliary supporting structure are arranged at both ends of the opening, respectively.

11. The radiotherapy system according to claim 10, wherein the auxiliary supporting structure is fixed with the radiological device.

12. The radiotherapy system according to claim 10, wherein the auxiliary supporting structure is located outside the opening.

13. The radiotherapy system according to claim 10, wherein the auxiliary supporting structure is located inside the opening.

14. The radiotherapy system according to claim 10, wherein the main supporting structure is fixed with the radiological device.

15. The radiotherapy system according to claim 10, wherein the main supporting structure and the radiological device are arranged independently of each other.

\* \* \* \* \*